United States Patent [19]

Carr et al.

[11] Patent Number: 4,597,875

[45] Date of Patent: Jul. 1, 1986

[54] PRECIPITATIVE REMOVAL OF NITROCRESOLS FROM DINITROTOLUENE WASTE STREAMS

[75] Inventors: Richard V. C. Carr, Allentown; John E. Sawicki, Breinigsville; Bernard A. Toseland, Allentown, all of Pa.

[73] Assignee: Air Products and Chemicals, Inc., Allentown, Pa.

[21] Appl. No.: 731,424

[22] Filed: May 7, 1985

[51] Int. Cl.$^4$ .............................. C02F 1/52; C02F 1/66
[52] U.S. Cl. .................... 210/710; 210/712; 210/724; 210/726; 210/909; 568/932; 568/934
[58] Field of Search ............... 210/710, 712, 724, 726, 210/737, 769, 909; 568/927, 932, 934, 935

[56] References Cited

U.S. PATENT DOCUMENTS

| | | | |
|---|---|---|---|
| 2,647,084 | 7/1953 | McDonald | 210/909 |
| 3,458,435 | 7/1969 | Howe | 210/724 |
| 4,224,249 | 9/1980 | Kunz et al. | 260/580 |
| 4,230,567 | 10/1980 | Larbig | 210/600 |
| 4,361,712 | 11/1982 | Herman et al. | 568/932 |
| 4,482,769 | 11/1984 | Toseland et al. | 568/934 |

FOREIGN PATENT DOCUMENTS 1031450 10/1964 United Kingdom .

*Primary Examiner*—Peter Hruskoci
*Attorney, Agent, or Firm*—Russell L. Brewer; E. Eugene Innis; James C. Simons

[57] ABSTRACT

This invention relates to a process for removing nitrocresols and picric acid contaminants from a wastewater stream generated in the production of nitroaromatics, particularly dinitrotoluene, by the mixed acid technique. The process involves contacting the crude dinitrotoluene generated by the mixed acid technique with an alkaline medium to generate an alkaline wash water containing water soluble nitrocresols and picric acid therein. This wastewater is separated from the organic component and recycled for contact with further quantities of crude dinitrotoluene product from the reactor. When the concentration of the water soluble salts of nitrocresols and picric acid is of sufficient concentration the wash water is treated with aqueous acid in sufficient proportion to convert the water soluble salts to water insoluble organics. After treatment with acid, the organic material is separated from the wastewater and the organics incinerated.

7 Claims, No Drawings

PRECIPITATIVE REMOVAL OF NITROCRESOLS FROM DINITROTOLUENE WASTE STREAMS

TECHNICAL FIELD

This invention relates to an improved process for removing nitrocresols and organic water insoluble components from a nitroaromatic reaction product stream without generating an environmentally unacceptable aqueous discharge stream.

BACKGROUND OF THE INVENTION

Commercially, nitroaromatics, and particularly dinitrotoluene, are produced by the mixed acid nitration of toluene, the mixed acid being a mixture of concentrated sulfuric and concentrated nitric acid. In the production of dinitrotoluene process, for example, toluene is first nitrated to form mononitrotoluene and then separated from the spent acid aqueous phase. The crude mononitrotoluene is then dinitrated with fresh acid in a second nitration stage. As is known the dinitrotoluene product recovered from the dinitration reactor contains impurities, primarily nitrophenolics, such as nitrocresol and picric acid.

Traditionally, it has been common practice to remove the nitrophenolic materials from the organic dinitrotoluene phase because it has been believed they adversely affect the performance of hydrogenation catalysts in the reduction of dinitrotoluene to form toluenediamine. Removal of nitrophenolic material from the dinitrotoluene reaction product has been achieved by contacting that product with alkaline materials to convert the nitrophenolic materials with the crude dinitrotoluene reaction product to water soluble salts. The water soluble salts then are discharged.

Recent environmental regulations have placed severe restrictions on the discharge of aqueous streams containing alkali metal salts of nitrophenolic materials. As is known these materials are not readily subject to biodegradation and then there is an unknown factor regarding the toxicity of the materials in the amounts that would normally be discharged to the environment. Therefore it is desired that techniques be developed to remove nitrophenolic materials from a dinitrotoluene reaction product without creating an environmentally unacceptable aqueous discharge stream.

U.S. Pat. No. 4,482,769, although not prior art to this application, discloses a process for separating trinitroorthocresol from a reaction product while leaving dinitroorthocresol in the dinitrotoluene product. The process involves selectively precipitating the dinitroorthocresol from an aqueous stream by contacting with alkaline material.

Patents which show the removal of nitrophenolic material from crude dinitrotoluene streams by the addition of alkaline material are British Pat. No. 1,031,450; and U.S. Pat. Nos. 4,224,249; 4,361,712 and 4,230,567. Only the '567 patent addresses the problem of disposal of the wastewater streams containing alkali metal salts of nitrophenolic material. As acknowledged in that patent, direct incineration of the wastewater stream is considered to be energy intensive and is unacceptable for that reason. The approach taken in the '567 patent involves a degradation process as opposed to a combustion process.

SUMMARY OF THE INVENTION

This invention relates an improvement in a process for removing nitrophenolic material produced in the nitration of aromatic compounds by the mixed acid technique. The improvement resides in contacting the resultant crude nitroaromatic product with an alkaline material to convert nitrophenolic material therein to a water soluble salt, and thereby form a purified nitroaromatic organic water-insoluble product and an aqueous by-product phase containing the alkali metal salt of nitrophenolic materials, separating the aqueous phase from the organic phase, recycling a portion of the aqueous phase for contact with additional crude nitroaromatic product, increasing the concentration of water soluble salt of nitrophenolic material in said aqueous phase to a level from about 0.7 to 1.4% by weight, contacting the aqueous phase containing from 0.7 to 1.4% by weight of water soluble nitrophenolic material with an inorganic acid, said acid being added in sufficient proportion to convert the water soluble nitrophenolic material in said aqueous phase to water insoluble nitrophenolic, separating the aqueous phase from the converted nitrophenolic product and then incinerating the nitrophenolic material.

Advantages of the process include an ability to remove contaminant by-product from nitroaromatic production without creating an environmentally unacceptable waste stream; and an ability to remove contaminants in a nonenergy intensive manner.

DETAILED DESCRIPTION OF THE INVENTION

In the manufacture of nitroaromatics, particularly dinitrotoluene, the aromatic compound is contacted under liquid phase conditions with the mixture of concentrated nitric acid and sulfuric acid. In the production of nitroaromatics and particularly dinitrated products either dinitrobenzene or dinitrotoluene, some by-product nitrophenolic material is produced. This nitrophenolic material usually is in the form of nitrocresols either dinitro or trinitrocresol and picric acid. It is this product which is removed from the crude reaction product from the nitration reactors without creating an environmentally unacceptable stream.

In nitration processes the reaction product is removed from the nitration zone and passed to a separator where the organic phase is separated from the aqueous phase. According to the process herein, the crude nitroaromatic composition is contacted with a dilute aqueous alkaline-containing solution. Contact of the crude organic phase with alkaline material converts nitrocresols and picric acid to water soluble salts thereby generating an organic phase and an aqueous phase. Conventionally aqueous alkaline material suited for converting the nitrophenolic material to water soluble salts include sodium carbonate. ammonium hydroxide, sodium hydroxide, sodium bi-carbonate, potassium hydroxide, and other alkaline materials. Solution concentrations for achieving conversion to the water soluble salt generally are from about 0.1 to 50% by weight, and generally from about 1 to 10% by weight.

Contacting of the crude organic product with an aqueous alkaline solution is at a temperature from about 25° to 80° C. typically at atmospheric pressure to about 50 psig. Normally contacting is done at or about 25° C. and atmospheric pressure as this appears to be the most convenient way of converting the nitrophenolic materials to water soluble salts. Neither temperature nor pressure is critical to the conversion step.

Once the crude nitroaromatic composition has been treated with aqueous alkaline material, an organic layer and aqueous layer are formed. The aqueous layer is separated from the organic layer by decanting with the aqueous layer containing water soluble salts of nitrophenolic material; e.g., water soluble salts of dinitrocresol and trinitrocresol. To maximize the effectiveness of the alkaline treatment, the aqueous alkaline mixture after separation from the treated organic phase is recycled for contact with additional quantities of crude nitroaromatic product to enhance or increase the concentration of the water soluble salts in the aqueous phase and decrease the amount of unreacted aqueous alkaline material in that phase. Generally, the aqueous alkaline phase obtained on separation from the organic layer after nitration is recycled until the concentration of alkali metal salts of nitrophenolic material ranges from about 0.7 to 1.4% by weight usually 0.9–1.2% by weight.

When the concentration of water soluble nitrophenolic salt in the aqueous medium reaches from about 0.7 to 1.4%, at least a portion of the aqueous phase is separated for further treatment and disposal of the water-soluble salts of nitrophenolic material. In contrast to the prior art, the aqueous phase containing water-soluble nitrophenolic salt is treated with an acidic material under conditions sufficient to convert the water-soluble salt of the nitrophenolic material to a water-insoluble organic phase. This conversion can be accomplished by the addition of an inorganic acid such as nitric acid or sulfuric acid. Since both of these acids are available as spent acids from the nitration process, nitric acid and sulfuric acid are preferred. On addition of the acid at temperatures from about 25°–80° C. and atmospheric pressure to about 50 psig, typically 25°–30° C. and atmospheric pressure, the water-soluble salts of the nitrophenolic material are converted to a water-insoluble material. The water-insoluble material separates as an organic phase leaving an aqueous phase containing water-soluble salts.

The organic phase is separated from the aqueous phase after addition of the inorganic acid for permitting one to dispose of the contaminant nitrophenolic material. This contaminant, because of its low water content, can be incinerated under nonenergy intensive conditions. Incineration of the organic phase thereby removes nitrophenolic material as an environmentally unacceptable discharge.

The following examples are provided to illustrate various embodiments of the invention are not intended to restrict the scope thereof.

EXAMPLE 1

Alkali Washing of Dinitrotoluene

Into a one liter separatory funnel was placed 325 g of fresh water washed dinitrotoluene (trinitrocresol concentration of 1260 mg/kg) and 200 ml of 0.8 wt % sodium carbonate. The funnel was well shaken and the phrases allowed to separate while the temperature was maintained at 74° C. by placing the separatory funnel into a thermostated hot water bath. The separated organic phase was analyzed for trinitrocresols and about 20 ml of the aqueous phase was removed and discarded. The remainder of the aqueous phase was allowed to contact a second 325 g portion of fresh water washed dinitrotoluene in the separatory funnel and sufficient 6.0 wt % sodium carbonate (20–23 ml) was added to maintain a pH of the equilibrated mixture between 7.4 and 7.7. Samples were taken as above and the process repeated until ten 325 g portions of DNT had been washed. The amount of aqueous phase which was removed and discarded following each equilibration was sufficient to counterbalance the volume of fresh 6.0 wt % sodium carbonate which was added in the subsequent equilibration such that the volume of alkaline water in contact with the dinitrotoluene was always 200 ml.

The final alkaline wash solution which contained 1.13 wt % in trinitrocresols was adjusted to a pH of 1 by the addition of 40 ml of 20% sulfuric acid and the acidified mixture was allowed to stand and cool in a separatory funnel. Immediately following acidification, a dark liquid precipitate began to form and it settled out as a bottom phase over a period of three hours. The material (2.54 g) was removed and analyzed by liquid chromotography for trinitrocresols and by gas chromotography for nitrotoluene and dinitrotoluene (Table 1). From this analysis it may be determined that 88% of the 2.26 g of trinitrocresols in the final alkaline wash was removed as the liquid precipitate. The bottom product then was incinerated.

TABLE 1

Analysis of Liquid Precipitate from Alkaline Wash
Dry Weight Analysis

| Compound | Weight % |
| --- | --- |
| Trinitrocresols | 86.68 |
| Dinitrotoluene | 14.55 |
| Nitrotoluene | 0.02 |

*Sample contains 8.3% $H_2O$ by weight.

EXAMPLE 2

Batch Simulation of Continuous Countercurrent Alkaline Washing of Dinitrotoluene A batch simulation of a continuous countercurrent dinitrotoluene-alkaline wash extraction process was performed in a cascade of 250 ml separatory funnels. Dinitrotoluene containing 1222 ppm of trinitrocresols was submitted to this procedure using 3.73 wt % sodium carbonate for the aqueous alkaline feed and the aqueous to organic volume ratio was maintained at 0.078:1. Analyses of both the aqueous and organic phases following the simulated third countercurrent stage revealed a trinitrocresol content in the aqueous phase of 1.06 wt % and in the dinitrotoluene phase of 0.0592 wt %.

The distribution of trinitrocresols between the aqueous and organic phases was found to be 18:1 up to a maximum concentration of trinitrocresols in the aqueous phase of 1.4 wt %. Higher trinitrocresol concentrations in the aqueous phase increasingly cause the ratio to become smaller. After concentration, the nitrocresol was incinerated.

What is claimed:

1. In a process for removing nitrophenolic material from the crude nitroaromatic product produced in the nitration of aromatic compounds selected from the group consisting of dinitrobenzene and dinitrotoluene by the mixed acid technique, the improvement which resides in (a) contacting the resultant crude nitroaromatic product with an alkaline material to convert nitrophenolic material therein to a water soluble salt, and thereby form a purified nitroaromatic organic product and an aqueous by-product phase containing the alkali metal salt of nitrophenolic materials.

(b) separating the aqueous phase from the organic phase, (c) recycling a portion of the aqueous phase for contact with additional crude nitroaromatic product, and increasing the concentration of water soluble salt of nitrophenolic material in said aqueous phase to a level from about 0.7 to 1.4% by weight, (d) contacting the aqueous phase containing from 0.7 to 1.4% by weight of water soluble nitrophenolic material with an acid, said acid being added in sufficient proportion to convert the water soluble nitrophenolic material to water insoluble nitrophenolic organic phase, (e) separating the aqueous phase from the water insoluble nitrophenolic organic phase; and then (f) incinerating the nitrophenolic organic phase.

2. The process of claim 1 wherein the alkali metal used for washing the nitroaromatic is an aqueous solution of alkali metal carbonate; alkali metal bicarbonate; or alkali metal hydroxide.

3. The process of claim 2 wherein said nitroaromatic is dinitrotoluene.

4. The process of claim 3 wherein the alkali metal bicarbonate, alkali metal carbonate, or alkali metal hydroxide present in the aqueous solution is from about 1 to 10% by weight.

5. The process of claim 4 wherein the concentration of water soluble nitrophenolic material in the aqueous solution is from about 0.9 to 1.2% by weight prior to contact with acid.

6. The process of claim 5 wherein the acid used to neutralize the water soluble nitrophenolic salts is sulfuric acid or nitric acid.

7. The process of claim 6 wherein said alkali metal in said carbonate, bicarbonate and hydroxide is sodium.

* * * * *